US009931406B2

(12) United States Patent
Kim et al.

(10) Patent No.: US 9,931,406 B2
(45) Date of Patent: *Apr. 3, 2018

(54) PHARMACEUTICAL COMPOSITION COMPRISING AMIDE DERIVATIVE INHIBITING THE GROWTH OF CANCER CELLS AND NON-METALLIC SALT LUBRICANT

(71) Applicant: Hanmi Pharm. Co., Ltd., Gyeonggi-do (KR)

(72) Inventors: Yong Il Kim, Suwon-si (KR); Kyeong Soo Kim, Suwon-si (KR); Jin Cheul Kim, Eunpyeong-gu (KR); Yo Han Kim, Suwon (KR); Jae Hyun Park, Suwon-si (KR); Jong Soo Woo, Suwon-si (KR)

(73) Assignee: Hanmi Pharm. Co., Ltd., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/675,666

(22) Filed: Aug. 11, 2017

(65) Prior Publication Data

US 2017/0340744 A1 Nov. 30, 2017

Related U.S. Application Data

(63) Continuation of application No. 14/124,436, filed as application No. PCT/KR2012/003970 on May 18, 2012, now Pat. No. 9,731,022.

(30) Foreign Application Priority Data

Jun. 7, 2011 (KR) ........................ 10-2011-0054685

(51) Int. Cl.
```
A61K 31/517    (2006.01)
A61K 47/02     (2006.01)
A61K 47/06     (2006.01)
A61K 47/10     (2017.01)
A61K 47/12     (2006.01)
A61K 47/14     (2017.01)
A61K 47/26     (2006.01)
A61K 47/36     (2006.01)
A61K 47/44     (2017.01)
A61K 9/20      (2006.01)
C07D 401/12    (2006.01)
```

(52) U.S. Cl.
CPC ............ *A61K 47/44* (2013.01); *A61K 9/2013* (2013.01); *A61K 9/2018* (2013.01); *A61K 9/2077* (2013.01); *A61K 31/517* (2013.01); *A61K 47/02* (2013.01); *A61K 47/06* (2013.01); *A61K 47/10* (2013.01); *A61K 47/12* (2013.01); *A61K 47/14* (2013.01); *A61K 47/26* (2013.01); *A61K 47/36* (2013.01); *C07D 401/12* (2013.01); *A61K 9/2009* (2013.01); *A61K 9/2031* (2013.01)

(58) Field of Classification Search
CPC .. A61K 31/517; A61K 9/2009; A61K 9/2013; A61K 9/2018; A61K 9/2031; A61K 9/2077; A61K 47/02; A61K 47/06; A61K 47/14
See application file for complete search history.

(56) References Cited

U.S. PATENT DOCUMENTS

| | | | |
|---|---|---|---|
| 5,041,580 A | 8/1991 | Miyamoto et al. | |
| 8,188,102 B2 | 5/2012 | Lee et al. | |
| 8,859,767 B2 | 10/2014 | Bang et al. | |
| 2006/0088592 A1 | 4/2006 | Choi et al. | |
| 2007/0037837 A1 | 2/2007 | Hennequin et al. | |
| 2007/0135463 A1 | 6/2007 | Himmelsbach et al. | |
| 2008/0032996 A1 | 2/2008 | Mitsuya et al. | |
| 2010/0179120 A1 | 7/2010 | Lee et al. | |
| 2013/0071452 A1 | 3/2013 | Kim et al. | |

FOREIGN PATENT DOCUMENTS

| | | |
|---|---|---|
| ES | 2342965 T3 | 7/2010 |
| JP | H11349479 A | 12/1999 |
| JP | 2010529115 A | 8/2010 |
| JP | 2010-530890 A | 9/2010 |
| KR | 1019980008219 | 4/1998 |
| KR | 102000048572 | 7/2000 |
| KR | 1020020032612 | 5/2002 |
| KR | 10-2005-0104152 | 11/2005 |
| KR | 1020080107294 | 12/2008 |
| KR | 10-1013319 B1 | 2/2011 |
| RU | 2140782 C1 | 11/1999 |
| TW | 520364 B | 2/2003 |
| TW | 200906414 A | 2/2009 |
| WO | WO-98/13354 A1 | 4/1998 |
| WO | WO-02/18351 A1 | 3/2002 |
| WO | WO-02/18370 A1 | 3/2002 |

(Continued)

OTHER PUBLICATIONS

Anonymous, "Handbook of Pharmaceutical Excipients", 2006, Pharmaceutical Press, XP002736604, p. 767.
Anonymous, "The Merck Index", 2001, Merck & Co. Inc., XP002736605, p. 5682.
Anonymous, Handbook of Pharmaceutical Excipients, 2006 Pharmaceutical Press, XP002736604, p. 767.
Anonymous, The Merck Index, 2001, Merck & Co., Inc. XP002736605, p. 5682.
Article as to alginic acid published by Drug Topics (Oct. 2008).
Ballard et al., Inhibitors of epidermal growth factor receptor tyrosine kinase: optimisation of potency and in vivo pharmacokinetics, Bioorg. Med. Chem. Lett., 16(18):4908-12 (2006).

(Continued)

*Primary Examiner* — John Pak
*Assistant Examiner* — Nathan W Schlientz
(74) *Attorney, Agent, or Firm* — Marshall, Gerstein & Borun LLP (57) ABSTRACT

Disclosed is a pharmaceutical composition comprising an amide derivative or a pharmaceutically acceptable salt thereof and a non-metallic salt lubricant, which can be used as an effective cancer cell-growth inhibitor owing to its enhanced storage stability with no quality changes over time.

18 Claims, 2 Drawing Sheets

(56) References Cited

FOREIGN PATENT DOCUMENTS

| WO | WO-03/82290 A1 | 10/2003 |
|---|---|---|
| WO | WO-2005/030757 A1 | 4/2005 |
| WO | WO-2005/030765 A1 | 4/2005 |
| WO | WO-2005/033096 A1 | 4/2005 |
| WO | WO-2005/090332 A1 | 9/2005 |
| WO | WO-2007/023073 A2 | 3/2007 |
| WO | WO-2007/118854 A1 | 10/2007 |
| WO | WO-2008/150118 A2 | 12/2008 |
| WO | WO-2009/002826 A2 | 12/2008 |
| WO | WO-2010/123340 A1 | 10/2010 |
| WO | WO-2011/088149 A2 | 7/2011 |
| WO | WO-2011/155793 A2 | 12/2011 |
| WO | WO-2012/169733 A1 | 12/2012 |
| WO | WO-2013/051883 A2 | 4/2013 |

OTHER PUBLICATIONS

Cha et al., Antitumor activity of HM781-36B, a highly effective pan-H ER inhibitor in erlotinib-resistant NSCLC and other EGFR-dependent cancer models, Int. J. Cancer, 130(10):2445-54 (2012).
Denny, Irreversible inhibitors of the erbB family of protein tyrosine kinases, Pharm. Therapeutics, 83(2-3):253-61 (2002).
Eriksson et al., Synthesis of [11C]/[13C]acrylamides by palladium-mediated carbonylation, Eur. J. Org. Chem., 2007(3):455-61 (2007).
European Patent Office, Communication dated Mar. 16, 2015, issued in corresponding European Application No. 12796126.6.
Extended European Search Report, European patent application No. 14743689.3, dated Jun. 7, 2016.
International Preliminary Report on Patentability, International Application No. PCT/KR2014/000752, dated Jul. 28, 2015.
International Search Report and Written Opinion, International Application No. PCT/KR2014/000752, dated May 9, 2014.
International Searching Authority, of PCT/KR2012/003970, dated Nov. 9, 2012.
Japanese Patent Office, Communication dated Feb. 9, 2016 issued in corresponding Application No. 2014-51470.
Nam et al., Antitumor activity of HM781-36B, an irreversible Pan-HER inhibitor, alone or in combination with cytotoxic chemotherapeutic agents in gastric cancer, Cancer Lett., 302 (2011) 155-165.
Nam et al., Antitumor activity of HM781-36B, an irreversible Pan-HER inhibitor, alone or in combination with cytotoxic chemotherapeutic agents in gastric cancer, Cancer Lett., 302:155-65 (2011).
Pharmaceutical excipients including alginic acid published by International Cenological Codex (Apr. 10, 2010).
Pharmaceutics Manual (the 2nd edition), Namsandang: 83, 84, 110 & 120 (1998), 14 pages total.
Pharmaceutics Manual (the 2nd edition), Namsandang: pp. 83, 84, 110, 120 (1998).
Republic of Colombia Superintendence of Industry and Commerce, Communication dated Sep. 30, 2015, issued in corresponding Colombian Application No. PCT/14-000880.
Smaill et al., Tyrosine kinase inhibitors. 15. 4-(Phenylamino)quinazoline and 4-(Phenylamino)pyrido[d]pyrimidine Acrylamides as Irreversible inhibitors of the ATP binding site of the epidermal growth factor receptor, J. Med. Chem., 42:1803-15 (1999).
Thoma et al., Enteric coated hard gelatin capsules, Department of Pharmaceutical Technology, Ludwig Maximillian University, 8000 Munich 2, Germany, published in 2000.

PHARMACEUTICAL COMPOSITION COMPRISING AMIDE DERIVATIVE INHIBITING THE GROWTH OF CANCER CELLS AND NON-METALLIC SALT LUBRICANT

CROSS-REFERENCE TO RELATED APPLICATION

This application is a continuation of U.S. patent application Ser. No. 14/124,436, filed Dec. 6, 2013, which is the U.S. national phase of PCT Application No. PCT/KR2012/003970, filed on May 18, 2012, which claims priority to Korean Patent Application No. 10-2011-0054685, filed on Jun. 7, 2011, the entire disclosures of which are hereby incorporated by reference in their entirety.

FIELD OF THE INVENTION

The present invention relates to a pharmaceutical composition comprising an amide derivative or its pharmaceutically acceptable salt inhibiting the growth of cancer cells and a non-metallic salt lubricant.

BACKGROUND OF THE INVENTION

The epidermal growth factor receptor (EGFR) is known to have four receptor subtypes, i.e., EGFR/ErbB1, Her-2/ErbB2, Her-3/ErbB3, and Her-4/ErbB4. They are abnormally overexpressed in most solid tumor cells. Also, activation of the receptor by ligands leads to activation of the cellular signaling pathway, which gives rise to growth, differentiation, angiogenesis, metastasis, and resistance of tumor cells (A. Wells, *Int. J. Biochem. Cell Biol.*, 1999, 31, 637-643). Therefore, it is expected that blocking of the tumor cell signaling pathway mediated by the epidermal growth factor receptor would produce antitumor effects. Hence, there have been many research efforts for developing anticancer drugs targeting the epidermal growth factor receptor.

Such anticancer drugs targeting the epidermal growth factor receptor are categorized into two groups: monoclonal antibodies targeting an extracellular domain and small molecule drugs targeting an intracellular tyrosine kinase. The monoclonal antibodies have an advantage of a good pharmaceutical efficacy with a less extent of side effects due to its selective binding on the epidermal growth factor receptors. However, the monoclonal antibodies have drawbacks that they are quite expensive and must be administered by injection. Meanwhile, the small molecule drugs targeting a tyrosine kinase are relatively inexpensive and orally administrable, and they also have a good pharmaceutical efficacy through reacting with the receptor subtypes (e.g., EGFR, Her-2, Her-3 and Her-4) selectively or simultaneously.

Examples of the small molecule drugs include selective inhibitors of EGFR such as Iressa® (Gefitinib, AstraZenaca) and Tarceva® (Erlotinib, Roche), and dual inhibitors simultaneously blocking EGFR and Her-2 such as Tykerb® (Lapatinib, GlaxoSmithKline). These drugs are currently being used for treating lung cancer and advanced Her-2 positive breast cancer, respectively. Clinical trials therefor are also being conducted to increase the efficacy against other solid tumors.

A recent study has reported that a second mutation—i.e., a threonine-to-methionine substitution at the amino acid position 790 in adenosine triphosphate (ATP)-binding sites to the EGFR tyrosin kinase domain—can reduce the binding ability of the drug, which results in a drastic decrease in the drug response rate (C. H. Gow, et al., *PLoS Med.*, 2005, 2(9), e269). Thus, it is required to develop a drug having enhanced inhibitory activities against EGFR resistant cancer cells.

Korean Patent Laid-open Publication No. 2008-0107294 discloses a compound of formula (I), which selectively and effectively inhibits the growth of cancer cells and the development of drug resistance induced by the EGFR and its mutants without side effects. However, it has been found that the pharmaceutical formulation comprising the compound of formula (I) as an active ingredient and its pharmaceutically acceptable additives facilitates the formation of a compound of formula (II) (hereinafter, referred to as the related compound IV) under certain storage conditions, thereby reducing the amount of the compound of formula (I).

The purity of an active ingredient is an important factor for preparing a safe and effective pharmaceutical composition because certain impurities contained in a drug substance may produce side effects during treatment. Some of the impurities can be removed during the preparation of the drug. But certain materials produced by degradation of the drug due to the changes in such various conditions as temperature, humidity and light may remain as impurities.

The present inventors have endeavored to study the factors that promote the formation of the related compound IV during storage of a pharmaceutical formulation comprising a compound of formula (I) and have found that pharmaceutically acceptable additives, particularly metallic salts contained in lubricants, cause expedition of the formation of the related compound IV. Hence, the present inventors have developed a pharmaceutical composition having an enhanced stability by employing a non-metallic salt lubricant, which is free of a metallic salt component.

SUMMARY OF THE INVENTION

It is an object of the present invention to provide a pharmaceutical composition with an improved stability, comprising an amide derivative or a pharmaceutically acceptable salt thereof, which effectively inhibits the growth of cancer cells.

In accordance with one aspect of the present invention, there is provided a pharmaceutical composition comprising a compound of formula (I) or a pharmaceutically acceptable salt thereof, and a non-metallic salt lubricant:

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The present invention provides a pharmaceutical composition comprising a compound of formula (I) or a pharmaceutically acceptable salt thereof, and a non-metallic salt lubricant:

Each ingredient of the inventive pharmaceutical composition is described in detail as follows.

(A) Pharmaceutically Active Ingredient

The pharmaceutical composition according to the present invention comprises a compound of formula (I) or a pharmaceutically acceptable salt thereof as a pharmaceutically active ingredient.

The compound of formula (I) (hereinafter referred to as the code name "HM781-36B"), as disclosed in Korea Patent Laid-open Publication No. 2008-0107294, can selectively and effectively inhibit the growth of cancer cells and the development of drug resistance induced by the EGFR and its mutants, while causing no adverse side effects.

The pharmaceutically acceptable salt of the compound of formula (I) includes, but is not limited to, an acid-addition salt of an inorganic or organic acid. Examples of the inorganic acid-addition salt may include salts of hydrochloric acid, sulfuric acid, disulfonic acid, nitric acid, phosphoric acid, perchloric acid, or bromic acid; examples of the organic acid-addition salt may include salts of formic acid, acetic acid, propionic acid, oxalic acid, succinic acid, benzoic acid, citric acid, maleic acid, malonic acid, malic acid, tartaric acid, gluconic acid, lactic acid, gestisic acid, fumaric acid, lactobionic acid, salicylic acid, phthalic acid, embonic acid, aspartic acid, glutamic acid, camsylic acid, besylic acid, or acetylsalicylic acid (aspirin). The pharmaceutically acceptable salt may also include metal salts derived from alkali metals such as calcium, sodium, magnesium, strontium, potassium, and the like.

In the present invention, the compound of formula (I) may be employed in an amount ranging from 0.1 to 50% by weight, preferably 0.5 to 10% by weight, based on the total weight of the composition. The compound may be contained in the composition in an amount ranging from 0.1 mg to 100 mg, preferably 0.5 to 50 mg, per 1 dosage unit of the composition.

(B) Non-Metallic Salt Lubricant

Lubricants are ingredients added to improve the compression process of granules, and they are considered as a critical excipient, which plays important roles in the manufacture of solid compressed compositions. Advantages of employing lubricants include an improved flow of the powder or granular materials, which allows them to be more readily filled in a die; a reduced friction of the powder or granular materials as well as that between the powder or granular materials and the punch or the die; and enhanced compressibility and dischargeability of the tablets. Lubricants can be categorized as shown in Table 1.

TABLE 1

| Category | Lubricant |
|---|---|
| Fatty acid metal salts | calcium stearate, magnesium stearate, sodium stearyl fumarate, zinc stearate |
| Fatty acid esters | glyceryl behenate, glyceryl palmitostearate, glyceryl monostearate, glyceryl trimyristate, glyceryl tristearate, sucrose fatty acid ester |
| Fatty acids & alcohols | palmitic acid, palmitoyl alcohol, stearic acid, stearyl alcohol |
| Oils | hydrogenated castor oil, mineral oil, hydrogenated vegetable oil |
| Others | fumaric acid, polyethylene glycol (PEG 4000 & PEG 6000), polytetrafluoroethylene, talc |

The pharmaceutical composition of the present invention comprising a compound of formula (I) is characterized by the use of a non-metallic salt lubricant in order to prevent the formation of the related compound IV, which may otherwise be formed due to a metallic salt if it is contained in the composition.

The term "non-metallic salt lubricant" according to the present invention refers to a lubricant that is free of metallic materials, e.g., such metallic salts as calcium stearate, magnesium stearate, sodium stearayl fumarate, zinc stearate, and the like. Examples of the non-metallic salt lubricant according to the present invention may include fatty acid esters, fatty acids, fatty alcohols, oils, fumaric acid, polyethylene glycols (PEGs), polytetrafluoroethylenes, starch, talc, and the like. The enhanced storage stability of the inventive pharmaceutical composition can be achieved by employing such non-metallic salt lubricants.

Specifically, examples of the non-metallic salt lubricant, which can be used in the present invention, may include, but are not limited to, fatty acid esters (e.g., glyceryl behenate, glyceryl palmitostearate, glyceryl monostearate, glyceryl trimyristate, glyceryl tristearate, sucrose fatty acid ester, and the like); fatty acids and fatty alcohols (e.g., palmitic acid, palmitoyl alcohol, stearic acid, stearyl alcohol, and the like); oils (e.g., hydrogenated castor oil, mineral oil, hydrogenated vegetable oil, and the like); fumaric acid; polyethylene glycol (e.g., PEG 4000 or PEG 6000); polytetrafluoroethylene; starch; and talc. The non-metallic salt lubricants may be used solely or as a mixture thereof.

Preferably, exemplary non-metallic salt lubricants according to the present invention may include sucrose fatty acid ester, hydrogenated vegetable oil, stearic acid, glyceryl behenate, glyceryl palmitostearate, talc, starch, and PEG 6000, more preferably sucrose fatty acid ester and hydrogenated vegetable oil.

In the present invention, the non-metallic salt lubricant may be employed in an amount ranging from 0.1 to 100 parts by weight, preferably 0.1 to 50 parts by weight, more preferably 0.25 to 10 parts by weight, based on 1 part by weight of the compound of formula (I).

If the amount of the non-metallic salt lubricant employed is less than 0.1 parts by weight, a tablet formed would not be readily released from the die cast or may stick to the die cast during the tablet formation. On the other hand, if the amount is greater than 100 parts by weight, a tablet would suffer from such problems as capping or delamination. Moreover, since lubricants are in general hydrophobic, if they are employed in a large amount, they may cause such unintended problems as a delayed disintegration and a low dissolution rate.

(C) Pharmaceutically Acceptable Additives

The pharmaceutical composition of the present invention may further comprise pharmaceutically acceptable additives and can be formulated into a variety of administration forms, preferably an oral administration form. Representative examples of the formulation for oral administration may include powder, tablet, pill, capsule, liquid, suspension, emulsion, syrup, and granule, preferably tablet and capsule, but are not limited thereto.

In the present invention, the pharmaceutically acceptable additives may include a diluent, a binder, a disintegrant, and the like.

Examples of the diluent may include microcrystalline cellulose, lactose, mannitol, calcium phosphate, and the like; examples of the binder may include povidone, hydroxypropyl cellulose (HPC), hydroxypropyl methylcellulose (HPMC), polyvinyl alcohol (PVA), sodium carboxymethyl cellulose, and the like; and examples of the disintegrant may include crospovidone, sodium croscarmellose, sodium starch glycolate, and the like.

The diluent may be used in an amount ranging from 20 to 95% by weight, the binder may be used in an amount ranging from 1 to 10% by weight, and the disintegrant may be used in an amount ranging from 1 to 30% by weight, based on the total weight of the composition.

The pharmaceutical composition of the present invention may be coated with a coating substrate to prevent the composition from being in direct contact with the hand or skin of a user.

The coating substrate that can be used in the present invention may include a rapid release coating substrate, an enteric coating substrate, or a sustained release coating substrate. The rapid release coating substrate may be selected from the group consisting of hydroxypropyl cellulose, hydroxypropyl methylcellulose, polyvinyl alcohol, polyvinyl alcohol-polyethylene glycol graft polymer (Kollocoat IR®, BASF), and a mixture thereof. The enteric coating substrate may be selected from the group consisting of (meth)acrylate copolymer (Eudragit®, EVONIK), hydroxypropyl methylcellulose phthalate, cellulose acetate phthalate, and a mixture thereof. The sustained release coating substrate may be selected from the group consisting of cellulose acetate, ethyl cellulose, polyvinyl acetate, and a mixture thereof.

The coating substrate may be coated on the surface of the composition in an amount ranging from 1 to 50 parts by weight, preferably 1 to 30 parts by weight, based on 100 parts by weight of the uncoated core.

The present invention also provides a method for preparing the pharmaceutical composition comprising a compound of formula (I) or a pharmaceutically acceptable salt thereof and a non-metallic salt lubricant.

A formulation of the pharmaceutical composition comprising the above-mentioned ingredients can be prepared by the following method, which comprises the steps of:

(1) mixing a compound of formula (I) or a pharmaceutically acceptable salt thereof with such a pharmaceutically acceptable additive as a diluent and a binder, and granulating the mixture to obtain granules;

(2) mixing the granules prepared in step (1) with such a pharmaceutically acceptable additive as a diluent and a disintegrant, and adding a non-metallic salt lubricant thereto to obtain mixed granules; and (3) subjecting the mixed granules prepared in step (2) to a formulating step.

In one embodiment of the present invention, the inventive pharmaceutical composition can be prepared by admixing a compound of formula (I) and mannitol in a solution of povidone in purified water, subjecting the prepared mixture to wet granulation, and then drying the resulting granules. The prepared granules can be formed into a tablet by mixing the prepared granules with mannitol and Crospovidone, adding a non-metallic salt lubricant thereto, and then tableting the mixed granules by a tablet machine.

The various steps related with the formulation of the pharmaceutical composition of the present invention can be conducted according to conventional techniques known in the art. Further, the method of the present invention may further comprise the step of coating the formulation prepared in step (3) with the above-mentioned coating substrates for convenient storage and ease of use.

The pharmaceutical composition of the present invention can effectively inhibit the growth of cancer cells by comprising the compound of formula (I), which selectively and effectively inhibits the growth of cancer cells and the development of drug resistance induced by the EGFR and its mutants. Also, the pharmaceutical composition of the present invention can inhibit the formation of impurities (i.e., the related compounds IV) to less than 0.5% by weight under extreme conditions (e.g., kept in an airtight HDPE container at 60° C. for 4 weeks), and under accelerated conditions (e.g., kept in an airtight HDPE container at 40° C./75% RH for 6 months) by comprising the non-metallic salt lubricant. Therefore, the pharmaceutical composition of the present invention can enhance the efficacy and improve the stability of the compound of formula (I).

Therefore, the present invention provides a method to stabilize a pharmaceutical composition comprising the compound of formula (I) or a pharmaceutically acceptable salt thereof, comprising adding the non-metallic salt lubricant to the pharmaceutical composition.

The following Examples are intended to further illustrate the present invention without limiting its scope.

EXAMPLES

Examples 1 to 8: Preparation of Pharmaceutical Compositions Comprising Non-Metallic Salt Lubricants Pharmaceutical compositions of Examples 1 to 3 were prepared by employing a compound of formula (I) (hereinafter, referred to as "HM781-36B," Dongwoo Syntech Co., Ltd., Korea); mannitol (Roquette); Povidone® (BASF); Crospovidone® (BASF); and sucrose fatty acid ester (Daiichi Kogyo Seiyaku, Japan), hydrogenated vegetable oil (Lubritab®, JRS Pharma), or stearic acid (Emery Oleochemicals.), as a non-metallic salt lubricant, in accordance with the composition and the amount (unit: mg) described in Table 2.

Specifically, HM781-36B and mannitol were mixed and the mixture was subjected to a wet-granulation process by a conventional method with employing a binder solution of Povidone dissolved in purified water. The wet granules thus obtained were dried, mixed with mannitol and Crospovidone, and subsequently added with a lubricant, which was previously sieved through a 30 mesh screen, to prepare a final mixture. The final mixture thus prepared was formed into a tablet having a hardness of about 5 to 10 kp by a tablet machine (Sejong, Korea) according to a conventional method.

TABLE 2

|  |  |  | Ex. 1 | Ex. 2 | Ex. 3 |
|---|---|---|---|---|---|
| Wet granule | Mixture | HM781-36B | 0.5 | 0.5 | 0.5 |
|  |  | Mannitol | 50 | 50 | 50 |
|  | Binder | Povidone | 1.5 | 1.5 | 1.5 |
|  |  | <Purified water> | <10> | <10> | <10> |

TABLE 2-continued

|  |  | Ex. 1 | Ex. 2 | Ex. 3 |
|---|---|---|---|---|
| Mixture | Mannitol | 42 | 42 | 42 |
|  | Crospovidone | 5 | 5 | 5 |
| Final mixture | Sucrose fatty acid ester | 2 | — | — |
|  | Hydrogenated vegetable oil | — | 2 | — |
|  | Stearic acid | — | — | 1 |
| Total weight |  | 101 | 101 | 100 |

Pharmaceutical compositions of Examples 4 to 8 were prepared by the same method as above by employing a compound of formula (I) (HM781-36B, Dongwoo Syntech Co., Ltd., Korea); mannitol (Roquette); Povidone® (BASF); Crospovidone® (BASF); and glyceryl behenate (Compritol 888 ATO®, Gattefosse), glyceryl palmitostearate (Compritol HD5®, Gatefosse), talc (Nippon Talc Corp., Japan), starch (Roquette), or PEG 6000 (Sanyo Chemical, Japan), as a non-metallic salt lubricant, in accordance with the composition and the amount (unit: mg) described in Table 3.

TABLE 3

|  |  |  | Ex. 4 | Ex. 5 | Ex. 6 | Ex. 7 | Ex. 8 |
|---|---|---|---|---|---|---|---|
| Wet granule | Mixture | HM781-36B | 0.5 | 0.5 | 0.5 | 0.5 | 0.5 |
|  |  | Mannitol | 50 | 50 | 50 | 50 | 50 |
|  | Binder | Povidone | 1.5 | 1.5 | 1.5 | 1.5 | 1.5 |
|  |  | <Purified water> | <10> | <10> | <10> | <10> | <10> |
|  | Mixture | Mannitol | 42 | 42 | 42 | 42 | 42 |
|  |  | Crospovidone | 5 | 5 | 5 | 5 | 5 |
| Final mixture |  | Glyceryl behenate | 2 | — | — | — | — |
|  |  | Glyceryl palmitostearate | — | 2 | — | — | — |
|  |  | Talc | — | — | 3 | — | — |
|  |  | Starch | — | — | — | 5 | — |
|  |  | PEG 6000 | — | — | — | — | 3 |
| Total weight |  |  | 101 | 101 | 102 | 104 | 102 |

Pharmaceutical compositions of Examples 9 to 15 were prepared by the same method as above by employing a compound of formula (I) (HM781-36B, Dongwoo Syntech Co., Ltd., Korea); mannitol (Roquette); Povidone® (BASF); Crospovidone® (BASF); and glyceryl monostearate (Capmul GMS-50), palmitoyl alcohol (Landz International Company Ltd., China), stearyl alcohol (Lubrizol Advanced Materials, U.S.), hydrogenated castor oil (BASF), mineral oil (Alfa Aesar, U.S.), fumaric acid (Merck), or silicon dioxide (Grace Davison, U.S.), as a non-metallic salt lubricant, in accordance with the composition and the amount (unit: mg) described in Table 4.

TABLE 4

|  |  |  | Ex. 9 | Ex. 10 | Ex. 11 | Ex. 12 | Ex. 13 | Ex. 14 | Ex. 15 |
|---|---|---|---|---|---|---|---|---|---|
| Wet granule | Mixture | HM781-36B | 0.5 | 0.5 | 0.5 | 0.5 | 0.5 | 0.5 | 0.5 |
|  |  | Mannitol | 50 | 50 | 50 | 50 | 50 | 50 | 50 |
|  | Binder | Povidone | 1.5 | 1.5 | 1.5 | 1.5 | 1.5 | 1.5 | 1.5 |
|  |  | <Purified water> | <10> | <10> | <10> | <10> | <10> | <10> | <10> |
|  | Mixture | Mannitol | 42 | 42 | 42 | 42 | 42 | 42 | 42 |
|  |  | Crospovidone | 5 | 5 | 5 | 5 | 5 | 5 | 5 |
| Final mixture |  | Glyceryl monostearate | 5 | — | — | — | — | — | — |
|  |  | Palmitoyl alcohol | — | 5 | — | — | — | — | — |
|  |  | Stearyl alcohol | — | — | 5 | — | — | — | — |
|  |  | Hydrogenated castor oil | — | — | — | 5 | — | — | — |

TABLE 4-continued

|  | Ex. 9 | Ex. 10 | Ex. 11 | Ex. 12 | Ex. 13 | Ex. 14 | Ex. 15 |
|---|---|---|---|---|---|---|---|
| Mineral oil | — | — | — | — | 5 | — | — |
| Fumaric acid | — | — | — | — | — | 5 | — |
| Silicon dioxide | — | — | — | — | — | — | 2 |
| Total weight | 104 | 104 | 104 | 104 | 104 | 104 | 101 |

Comparative Examples 1 to 4: Preparation of Pharmaceutical Compositions Comprising Metallic Salt Lubricants The procedures of the above Examples were repeated by employing the composition and the amount (unit: mg) described in Table 5, to prepare pharmaceutical compositions of Comparative Examples 1 to 4 comprising metallic salt lubricants.

TABLE 5

|  |  |  | Comp. Ex. 1 | Comp. Ex. 2 | Comp. Ex. 3 | Comp. Ex. 4 |
|---|---|---|---|---|---|---|
| Wet granule | Mixture | HM781-36B | 0.5 | 0.5 | 0.5 | 0.5 |
|  |  | Mannitol | 50 | 50 | 50 | 50 |
|  | Binder | Povidone | 1.5 | 1.5 | 1.5 | 1.5 |
|  |  | <Purified water> | <10> | <10> | <10> | <10> |
| Mixture |  | Mannitol | 42 | 42 | 42 | 42 |
|  |  | Crospovidone | 5 | 5 | 5 | 5 |
| Final mixture |  | Magnesium stearate | 1 | — | — | — |
|  |  | Calcium-stearate | — | 1 | — | — |
|  |  | Sodium stearyl fumarate | — | — | 1 | — |
|  |  | Zinc stearate | — | — | — | 1 |
|  | Total weight |  | 100 | 100 | 100 | 100 |

Test Example: Measurement of the Related Compound Formed

Figure 1:
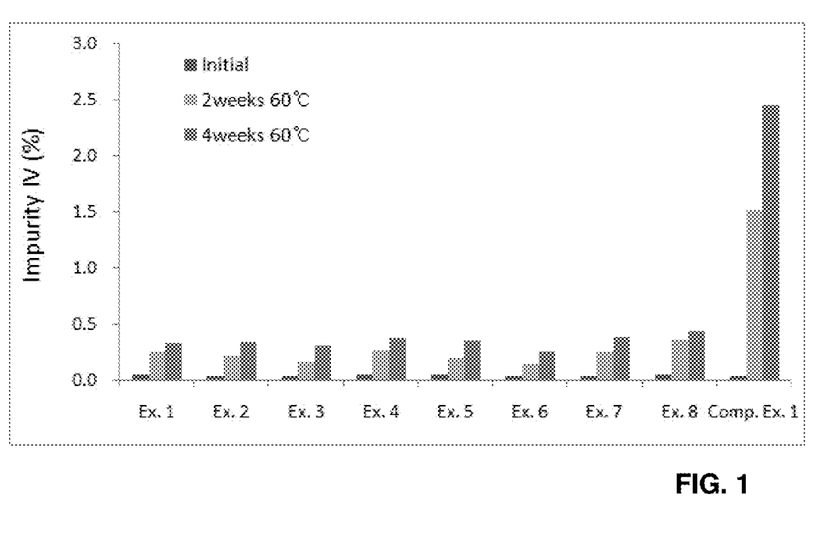
FIG. 1: the stability test results showing the amount of the related compound IV produced after heating the pharmaceutical compositions of Examples 1 to 8 and Comparative Example 1 at 60° C.
Figure 2:
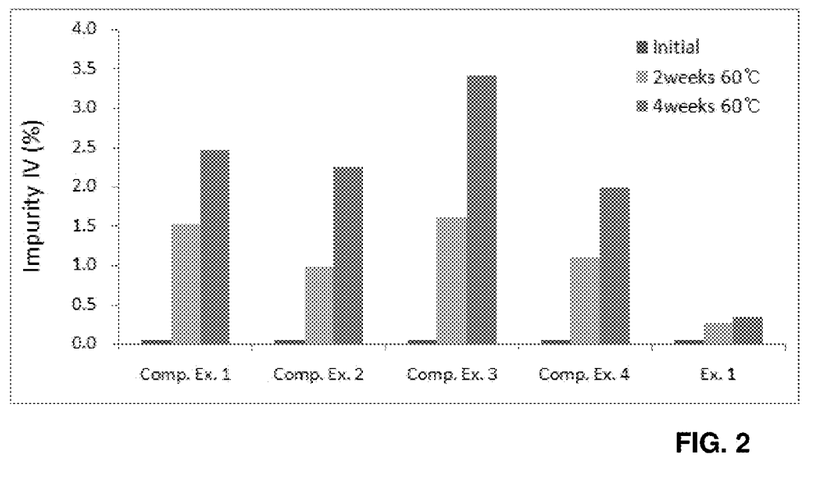
FIG. 2: the stability test results showing the amount of the related compound IV produced after heating the pharmaceutical compositions of Comparative Examples 1 to 4 and Example 1 at 60° C.

In order to evaluate the storage stability of the pharmaceutical compositions prepared in Examples 1 to 8 and Comparative Examples 1 to 4, the pharmaceutical compositions were each packaged with 1 g of silica gel in an HDPE bottle and stored in a chamber (60° C.). After 2 and 4 weeks, respectively, the related compound IV, a major degradation product of HM781-36B, was extracted by 60% acetonitrile as a solvent, and then HPLC analyses were performed. The results of Examples 1 to 8 are shown in Table 6 and FIG. 1, and those of Comparative Examples 1 to 4 are shown in Table 7 and FIG. 2.

TABLE 6

| Ex. | 1 | 2 | 3 | 4 | 5 | 6 | 7 | 8 |
|---|---|---|---|---|---|---|---|---|
| Initial | 0.05 | 0.04 | 0.04 | 0.05 | 0.05 | 0.04 | 0.04 | 0.05 |
| 2 weeks, 60° C. | 0.26 | 0.23 | 0.17 | 0.27 | 0.21 | 0.15 | 0.18 | 0.37 |
| 4 weeks, 60° C. | 0.34 | 0.35 | 0.31 | 0.38 | 0.36 | 0.26 | 0.29 | 0.45 |

TABLE 7

|  | Comp. Ex. 1 | Comp. Ex. 2 | Comp. Ex. 3 | Comp. Ex. 4 |
|---|---|---|---|---|
| Initial | 0.04 | 0.04 | 0.04 | 0.04 |
| 2 weeks, 60° C. | 1.52 | 0.98 | 1.60 | 1.09 |
| 4 weeks, 60° C. | 2.46 | 2.25 | 3.41 | 1.98 |

Figure 3:
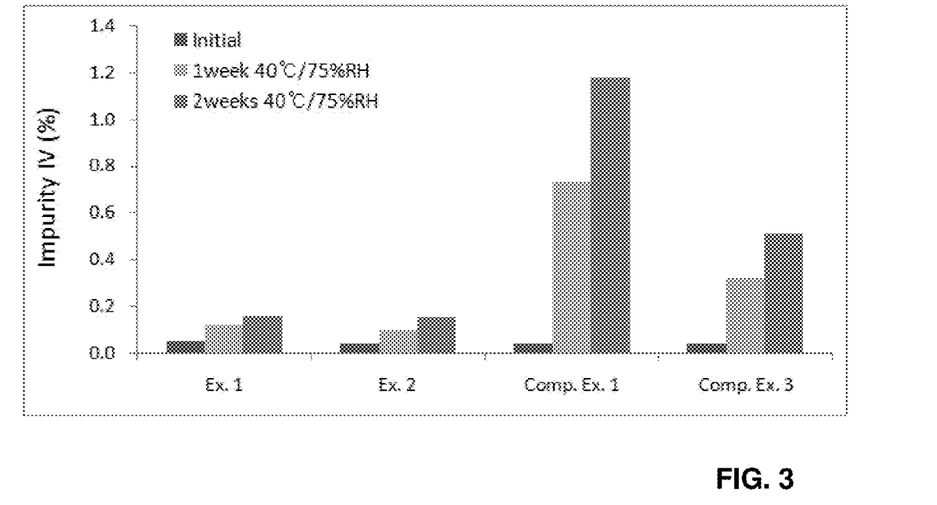
FIG. 3: the accelerated stability test results showing the amount of the related compound IV produced after exposure of the pharmaceutical compositions of Examples 1 and 2 and Comparative Examples 1 and 3 under the accelerated conditions (40° C. and 75% RH)

In order to observe the changes of stability of the pharmaceutical compositions prepared in accordance with Examples 1 and 2 and Comparative Examples 1 and 3 against temperature and humidity, the pharmaceutical compositions were exposed to 40° C. and 75% RH. After 1 and 2 weeks, respectively, the related compound IV, a major degradation product of HM781-36B, was extracted by 60% acetonitrile as a solvent, and then HPLC analyses were performed. The results are shown in Table 8 and FIG. 3.

TABLE 8

|  | Ex. 1 | Ex. 2 | Comp. Ex. 1 | Comp. Ex. 3 |
|---|---|---|---|---|
| Initial | 0.05 | 0.04 | 0.04 | 0.04 |
| 1 week 40° C./75% RH | 0.12 | 0.10 | 0.73 | 0.32 |
| 2 weeks 40° C./75% RH | 0.16 | 0.15 | 1.18 | 0.51 |

Figure 4:
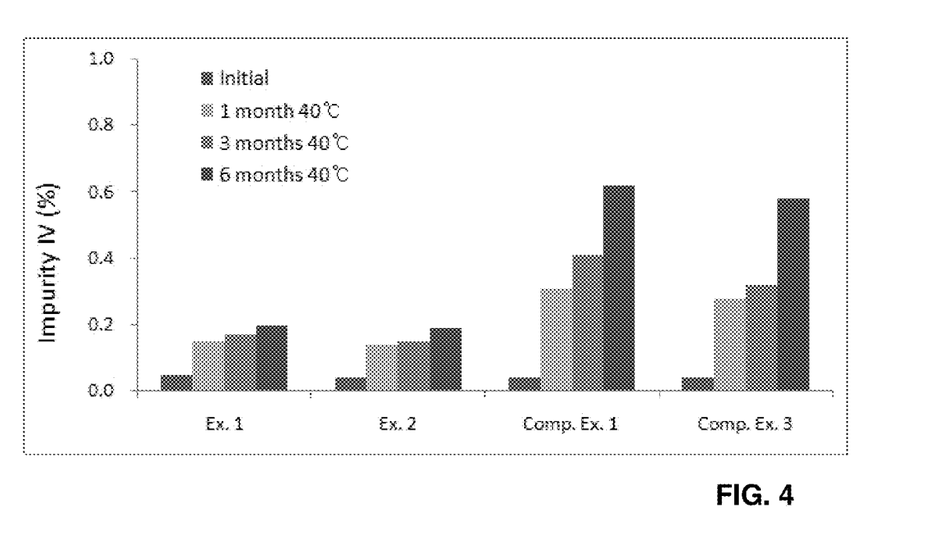
FIG. 4: the accelerated stability test results in a HDPE bottle showing the amount of the related compound IV produced after exposure of the pharmaceutical compositions of Examples 1 and 2 and Comparative Examples 1 and 3 under accelerated conditions (40° C. and 75% RH).

In order to observe the changes of stability of the pharmaceutical compositions prepared in accordance with Examples 1 and 2 and Comparative Examples 1 and 3 against temperature and humidity under accelerated conditions, the compositions were exposed to 40° C. and 75% RH in sealed HDPE containers for 1, 3 and 6 months. The related compound IV of each composition was extracted by 60% acetonitrile as a solvent, and then HPLC analyses were performed. The results are shown in Table 9 and FIG. 4.

TABLE 9

|  | Ex. 1 | Ex. 2 | Comp. Ex. 1 | Comp. Ex. 3 |
|---|---|---|---|---|
| Initial | 0.05 | 0.04 | 0.04 | 0.04 |
| 1 month ACLTD 40° C. | 0.15 | 0.14 | 0.31 | 0.28 |
| 3 months ACLTD 40° C. | 0.17 | 0.15 | 0.41 | 0.32 |
| 6 months ACLTD 40° C. | 0.20 | 0.18 | 0.62 | 0.58 |

As shown in Tables 6 to 9 and FIGS. 1 to 4, the formation of the related compound IV was reduced by about 4 to 10 times or more in the pharmaceutical compositions comprising any of the non-metallic salt lubricants compared with the pharmaceutical compositions comprising the metallic salt lubricants. Thus, the storage stability of the pharmaceutical compositions containing HM781-36B as an active ingredient can significantly be enhanced by adding any of the non-metallic salt lubricants to the pharmaceutical compositions.

According to the guidelines of the International Conference on Harmonisation of Technical Requirements for Registration of Pharmaceuticals for Human Use (ICH), the limits of unknown and known impurities are prescribed as 0.2% and 0.5%, respectively. The pharmaceutical compositions of Examples 1 and 2 according to the present invention showed satisfactory results of less than 0.5% at 40° C. in an accelerated stability test as described in the ICH guideline. In contrast, the pharmaceutical compositions of Comparative Examples 1 and 3 comprising conventional metallic salt lubricants exceeded the predetermined limits of the ICH guideline.

While the invention has been described with respect to the above specific embodiments, it should be recognized that various modifications and changes may be made to the invention by those skilled in the art which also fall within the scope of the invention as defined by the appended claims.

What is claimed is:

1. A pharmaceutical composition comprising a compound of formula (I) or a pharmaceutically acceptable salt thereof as an active ingredient and a non-metallic salt lubricant:

wherein the non-metallic salt lubricant is selected from the group consisting of talc, hydrogenated castor oil, mineral oil, hydrogenated vegetable oil, silicon dioxide, and a mixture thereof, wherein the composition is a solid compressed composition, and wherein the composition is free of metallic salt lubricants.

2. The pharmaceutical composition of claim 1, wherein said non-metallic salt lubricant is talc.

3. The pharmaceutical composition of claim 1, wherein said non-metallic salt lubricant is hydrogenated castor oil.

4. The pharmaceutical composition of claim 1, wherein said non-metallic salt lubricant is mineral oil.

5. The pharmaceutical composition of claim 1, wherein said non-metallic salt lubricant is hydrogenated vegetable oil.

6. The pharmaceutical composition of claim 1, wherein said non-metallic salt lubricant is silicon dioxide.

7. The pharmaceutical composition of claim 1, wherein said non-metallic salt lubricant is contained in an amount ranging from 0.1 to 100 parts by weight based on 1 part by weight of the compound of formula (I) or said pharmaceutically acceptable salt.

8. The pharmaceutical composition of claim 1, which further comprises a pharmaceutically acceptable additive selected from the group consisting of a diluent, a binder, a disintegrant, and a mixture thereof.

9. The pharmaceutical composition of claim 1, wherein the pharmaceutical composition further comprises a diluent in an amount ranging from 20% to 95% by weight based on the total weight of the composition.

10. The pharmaceutical composition of claim 1, wherein the pharmaceutical composition further comprises a binder in an amount ranging from 1% to 10% by weight based on the total weight of the composition.

11. The pharmaceutical composition of claim 1, wherein the pharmaceutical composition further comprises a disintegrant in an amount ranging from 1% to 30% by weight based on the total weight of the composition.

12. The pharmaceutical composition of claim 1, which is coated with a coating substrate selected from the group consisting of a rapid release coating substrate, an enteric coating substrate, and a sustained release coating substrate.

13. The pharmaceutical composition of claim 12, wherein said coating substrate is selected from the group consisting of hydroxypropyl cellulose, hydroxylpropyl methylcellulose, polyvinyl alcohol, polyvinyl alcohol-polyethylene glycol graft copolymer, (meth)acrylic acid copolymer, phthalic acid hydroxypropyl methylcellulose, phthalic acid cellulose acetate, cellulose acetate, ethyl cellulose, polyvinyl acetate, and a mixture thereof.

14. The pharmaceutical composition of claim 1, which comprises a compound of formula (II) in an amount less than 0.5% by weight under extreme conditions kept in an airtight HDPE container at 60° C. for 4 weeks, or under accelerated conditions kept in an airtight HDPE container at 40° C. and 75% RH for 6 months:

15. A unit dosage composition comprising the pharmaceutical composition of claim 1, wherein said compound of formula (I) or said pharmaceutically acceptable salt is contained in an amount ranging from 0.1 mg to 100 mg.

16. A method for preparing a formulation of the pharmaceutical composition, which comprises the steps of:
(1) mixing a compound of formula (I) or a pharmaceutically acceptable salt thereof with a pharmaceutically acceptable additive, and granulating the mixture to obtain granules;
(2) mixing the granules prepared in step (1) with a pharmaceutically acceptable additive, and adding a non-metallic salt lubricant thereto to obtain mixed granules; and
(3) subjecting the mixed granules prepared in step (2) to a compression step:

wherein the non-metallic salt lubricant is selected from the group consisting of talc, hydrogenated castor oil, mineral oil, hydrogenated vegetable oil, silicon dioxide, and a mixture thereof, wherein the composition is a solid compressed composition, and wherein the composition is free of metallic salt lubricants.

17. The method of claim 16, which further comprises the step of coating the formulation prepared in step (3) with a coating substrate selected from the group consisting of a rapid release coating substrate, an enteric coating substrate, and a sustained release coating substrate.

18. A method for stabilizing a pharmaceutical composition comprising a compound of formula (I) or a pharmaceutically acceptable salt thereof, comprising adding a non-metallic salt lubricant to the pharmaceutical composition:

wherein the non-metallic salt lubricant is selected from the group consisting of talc, hydrogenated castor oil, mineral oil, hydrogenated vegetable oil, silicon dioxide, and a mixture thereof, wherein the composition is a solid compressed composition, and wherein the composition is free of metallic salt lubricants.

* * * * *